(12) United States Patent
Assmann et al.

(10) Patent No.: US 6,486,191 B2
(45) Date of Patent: Nov. 26, 2002

(54) NITROPHENYL-SULPHONYL-IMIDAZOLES AND USE THEREOF FOR CONTROLLING VEGETABLE AND ANIMAL PESTS

(76) Inventors: Lutz Assmann, c/o Bayer Aktiengesellschaft, D 51368, Leverkusen (DE); Klaus Stenzel, c/o Bayer Aktiengesellschaft, D 51368, Leverkusen (DE); Christoph Erdelen, c/o Bayer Aktiengesellschaft, D 51368, Leverkusen (DE); Martin Kugler, c/o Bayer Aktiengesellschaft, D 51368, Leverkusen (DE); Peter Wachtler, c/o Bayer Aktiengesellschaft, D 51368, Leverkusen (DE)

( * ) Notice: Subject to any disclaimer, the term of this patent is extended or adjusted under 35 U.S.C. 154(b) by 0 days.

(21) Appl. No.: 09/990,493

(22) Filed: Nov. 16, 2001

(65) Prior Publication Data

US 2002/0094936 A1 Jul. 18, 2002

Related U.S. Application Data

(62) Division of application No. 09/774,229, filed on Jan. 30, 2001, now Pat. No. 6,350,770, which is a division of application No. 09/463,092, filed as application No. PCT/EP98/04326 on Jul. 13, 1998, now Pat. No. 6,262,100.

(30) Foreign Application Priority Data

Jul. 24, 1997 (DE) .......................... 197 31 781
Jul. 3, 1998 (DE) .......................... 198 29 740

(51) Int. Cl.⁷ ...................... G01N 43/50; C07D 233/54
(52) U.S. Cl. ................ 514/399; 548/335.5; 548/339.5; 548/340.1
(58) Field of Search ............................ 548/335.5, 339.5, 548/340.1; 514/399

(56) References Cited

FOREIGN PATENT DOCUMENTS

| DE | 196 09 060 | 2/1997 |
| EP | 0 238 824 | 9/1987 |
| EP | 0 284 277 | 9/1988 |
| FR | 1 485 394 | 9/1967 |

OTHER PUBLICATIONS

Chem. Ber. 85, (month unavailable) 1952, pp. 1012–1022, Friedhelm Korte: Synthese purinähnlicher Heterocyclen.

J. Med. Chem. 34 (month unavailable) 1991, pp. 1110–1116, Jung et al, Synthesis and Structure–Activity Relationship of New Cephalosporins with Amino Heterocycles at C–7. Dependence of the Antibacterial Spectrum and β–Lactamase Stability on the $pK_a$ of the C–7 Heterocycle.

J. Chem. Soc., (month unavailable) 1965, pp. 3017–3022, Barlin et al, Nucleophilic Displacement Reactions in Aromatic Systems, Part IX. ¹Kinetics of Reactions of 2–, 6–, or 8–Chloro–9–methylpurine with Piperidine in Ethanol.

Chemical Abstracts, vol. 116, No. 13, Mar. 30, 1992, Columbus, Ohio, U.S.; Abstract No. 123311y, Seite 328; CP002083855, siehe Zusammenfassung & JP 03 246206 A (Sumitomo Chemical Co., Ltd) Nov. 1, 1991.

Chemical Abstracts, vol. 117, No. 3, Jul. 20, 1992, Columbus, Ohio, U.S.; abstract no. 21974v, Seite 248, XP002083856, siehe Zusammenfassung & JP 04 029974 A (Sumitomo Chemical Co., Ltd) Jul. 20, 1992.

Primary Examiner—Patricia L. Morris

(57) ABSTRACT

Novel nitrophenyl-sulphonyl-imidazole of the formula (I)

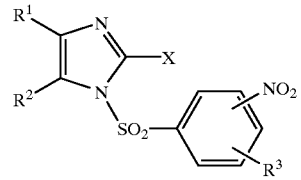

wherein X, $R^1$, $R^2$ and $R^3$ have the meanings stated in the description, a process for the preparation of the novel substances and their use for controlling vegetable and animal pests.

5 Claims, No Drawings

NITROPHENYL-SULPHONYL-IMIDAZOLES AND USE THEREOF FOR CONTROLLING VEGETABLE AND ANIMAL PESTS

This a Divisional Application of Ser. No. 09/774,229, filed Jan. 30, 2001, now U.S. Pat. No. 6,350,770, which is a Divisional Application of Ser. No. 09/463,092, filed Jan. 18, 2000, which has issued as U.S. Pat. No. 6,262,100, which is a 371 of PCT/EP98/04326, filed Jul. 13, 1998.

TECHNICAL FIELD OF THE INVENTION

The present invention relates to novel nitrophenyl-sulphonyl-imidazoles, a process for their prepartion and their use for controlling vegetable and animal pests.

BACKGROUND OF THE INVENTION

It has already become known that specific phenylsulphonyl-imidazoles and phenylsulphonyl-benzimidazoles have fungicidal properties (cf. EP-A 0 238 824 and WO 97-06 171). Thus, 1-(2-methyl-5-nitro-phenylsulphony)-benzotriazole, 2-menthyl-1-(2-menthyl-5-nitro-phenylsulphony)-imidazole and 1-(2-methyl-5-nitro-phenylsulphonyl)-2-chloro-6,6-difluoro-[1,3]-dioxolo-[4,5-f]-benzimidazole can be used for controlling fungi. The activity of these substances is good but is unsatisfactory in some cases at low application rates.

DETAILED DESCRIPTION OF THE INVENTION

Novel nitrophenyl-sulphonyl-imidazoles of the formula

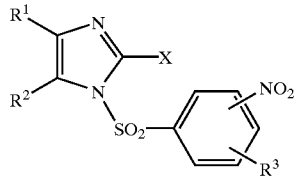

(I)

in which
a) X represents cyano,
  $R^1$ represents halogen, alkyl or phenyl,
  $R^2$ represents halogen, alkyl or phenyl or
  $R^1$ and $R^2$, together with the carbon atoms to which they are bonded, represent an optionally substituted benzene ring or represent an optionally substituted heterocyclic ring and
  $R^3$ represents halogen, alkyl or phenyl or
b) X represents halogen,
  $R^1$ represents halogen, alkyl or phenyl,
  $R^2$ represents halogen, alkyl or phlenyl or
  $R^1$ and $R^2$, together with the carbon atoms to which they are bonded, represent an optionally substituted heterocyclic ring or
  $R^1$ and $R^2$, together represent a doubly bonded radical of the formula

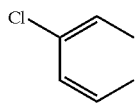 or 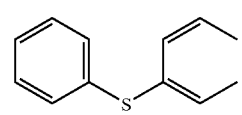

and
  $R^3$ represents halogen, alkyl or phenyl,
have now been found.

It has furthermore been found that nitrophenyl-sulphonyl-imidazoles of the formula (I) are obtained if imidazole derivatives of the formula

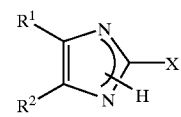

(II)

in which
$R^1$, $R^2$ and X have the abovementioned meanings,
are reacted with nitrobenzene-sulphonyl halides of the formula

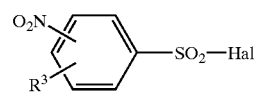

(III)

in which
$R^3$ has the abovementioned meaning and
Hal represents chlorine or bromine,
optionally in the presence of an acid acceptor and optionally in the presence of a dilueiit.

Finally, it has been found that the nitrophenyl-sulphonyl-imidazoles of the formula (I) are very suitable for controlling vegetable and animal pests in crop protection and in material protection.

Surprisingly, the substances according to the invention exhibit a better fungicidal activity than 1-(2-methyl-5-nitro-phenylsulphonyl)-benzotriazole and 2-methyl-1-(2-methyl-5-nitro-phienylsulphionyl)-imidazole, which are constitutionally similar, previously known active substances having the same type of activity.

The substances according to the invention are generally defined by the formula (I).

A preferred group of substances according to the invention are nitrophenyl-sulphonyl-imidazoles of the formula

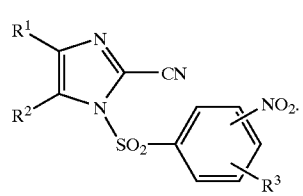

(Ia)

Here, the stibstituents preferably have the meanings stated below.

$R^1$ preferably represents fluorine, chlorine, bromine, straight-chain or branched alkyl having 1 to 6 carbon atoms or phenyl.

$R^2$ preferably represents fluorine, chlorine, bromine, straight-chain or branched alkyl having 1 to 6 carbon atoms or phenyl.

$R^1$ and $R^2$, together with the carbon atoms to which they are bonded, furthermore preferably represent a benzene ring which can be monosubstituted to trisubstituted, identically or differently, by
  halogen, cyano, nitro, formyl, carbamoyl, thiocarbamoyl;
  alkyl, alkoxy, alkylthio or alkylsulphonyl, each having 1 to 5 carbon atoms;

halogenoalkyl, halogenoalkoxy, halogenoalkylthio or halogenoalkylsulphonyl, each having 1 to 4 carbon atoms and 1 to 5 identical or different halogen atoms;

halogenioalkenyl or halogenoalkenyloxy, each of which is straight-chain or branched and each of which has 2 to 4 carbon atoms and 1 to 5 identical or different halogen atoms;

alkylcarbonyl, alkylcarbonyloxy, alkoxycarbonyl, alkylsulphonyloxy, hydrox-iminoalkyl, alkoximinoalkyl or cyanoimino(alkoxy)alkyl, each having 1 to 4 carbon atoms in the individual alkyl moieties;

cycloalkyl having 3 to 6 carbon atoms;

phenyl, phenoxy, phenylthio, pyridyl, pyridyloxy and/or pyridylthio, it being possible for each of these radicals to be monosubstituted or disubstituted, identically or differently, by halogen, cyano, nitro, alkyl having 1 to 4 carbon atoms and/or halogenoalkyl having 1 to 4 carbon atoms and 1 to 5 identical or different halogen atoms.

$R^1$ and $R^2$, together with the carbon atoms to which they are bonded, furthermore preferably represent a benzene ring which is substituted by doubly linked alkylene having 3 or 4 carbon atoms or dioxyalkylene having 1 or 2 carbon atoms, it being possible for the alkylene or dioxyalkylene groups to be monosubstituted to tetrasubstituted, identically or differently, by halogen, alkyl having 1 to 4 carbon atoms and/or halogenoalkyl having 1 or 2 carbon atoms and 1 to 5 identical or different halogen atoms.

$R^1$ and $R^2$, together with the carbon atoms to which they are bonded, furthermore preferably represent a 5- or 6-membered heterocyclic ring which contains one, two or three identical or different heteroatoms, such as oxygen, sulphur and/or nitrogen, and may be monosubstituted to trisubstituted, identically or differently, by halogen, cyano, nitro, hydroxyl, amino, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroximinoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety and/or halogenoalkylcarbonyloxy having 1 to 4 carbon atoms in the halogenoalkyl group and 1 to 5 identical or different halogen atoms, the oxygen atoms not being adjacent where the heterocyclic ring contains more than one oxygen atom.

$R^3$ preferably represents fluorine, chlorine, bromine, straight-chain or branched alkyl having 1 to 6 carbon atoms or phenyl.

A further group of preferred substances according to the invention are nitrophenyl-sulphonyl-imidazoles of the formula

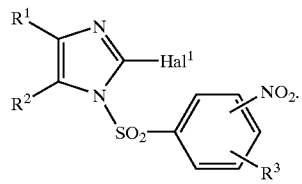

In this formula, the substituients preferably have the meanings stated below.

$Hal^1$ preferably represents fluorine, chlorine or bromine.

$R^1$ preferably represents fluorine, chlorine, bromine, straight-chain or branched alkyl having 1 to 6 carbon atoms or phenyl.

$R^2$ preferably represents fluorine, chlorine, bromine, straight-chain or branched alkyl having 1 to 6 carbon atoms or phenyl.

$R^1$ and $R^2$, together with the carbon atoms to which they are bonded, furthermore preferably represent a 5- or 6-membered heterocyclic ring which contains one, two or three identical or different heteroatoms, such as oxygen, sulphur and/or nitrogen, and may be monosubstituted to trisubstituted, identically or differently, by halogen, cyano, nitro, hydroxyl, amino, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsuiphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroximinoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety and/or halogenoalkylcarbonyloxy having 1 to 4 carbon atoms in the halogenoalkyl group having 1 to 5 identical or different halogen atoms, the oxygen atoms not being adjacent where the heterocyclic ring contains more than one oxygen atom $R^1$ and $R^2$ together furthermore preferably represent a doubly bonded radical of the formula

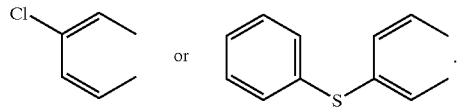

$R^3$ preferably represents fluorine, chlorine, bromine, straight-chain or branched alkyl having 1 to 6 carbon atoms or phenyl.

Particularly preferred are compounds of the formula (Ia), in which $R^1$ represents fluorine, chlorine, bromine, methyl, ethyl, n-propyl, isopropyl, n-butyl, secbutyl, iso-butyl, tert-butyl or phenyl, $R^2$ represents fluorine, chlorine, bromine, methyl, ethyl, n-propyl, isopropyl, n-butyl, sec-butyl, iso-butyl, tert-butyl or phenyl or $R^1$ and $R^2$, together with the carbon atoms to which they arc bonded, represent a benzene ring which may be monosubstituted to trisubstituted, identically or differently, by fluorine, chlorine, bromine, cyano, nitro, formyl, methyl, ethyl, n- or i-propyl, n-, i-, s- or t-butyl, methoxy, ethoxy, n- or i-propoxy, methyltillo, ethylthio, n- or i-propylthio, methylsulphonyl, ethylsulphoiiyl, trifluoromethyl, trifluoroethyl, difluoromethoxy, trifluoromethoxy, difluorochloromethoxy, trifluoroethoxy, difluoromethylthio, difluorochloromethylthio, trifluoromethiylthio, trifluoromethylsulphionyl, acetyl, propionyl, acetyloxy, methoxycarbonyl, ethoxycarbonyl, butoxycarbonyl, methylsulphonyloxy, etlylsulphonyloxy, hydroximinomethyl, hydroximinoethyl, methoximinomethyl, ethoximinoethyl, methoximinomethyl, ethoximinoethyl, cyanoimino (methoxy)methyl, cyclopropyl, cyclopentyl, cyclohexyl or phenyl, phenoxy, phenylthio, pyridyl, pyridyloxy and/ or pyridylthio, it being possible for each of these radicals to be monosubstituted or disubstituted, identically or differently, by fluorine, chlorine, bromine, cyano, nitro, methyl, ethyl, n-propyl, isopropyl, n-butyl, sec.-butyl, iso-butyl, tert-butyl, trifluoromethyl, trichloromethyl and/or difluoromethyl, or $R^1$ and $R^2$, together with the carbon atoms to which they are bonded, represent a benzene ring which is substituted by propane-1,3-diyl, butane-1,4-diyl, methylene-dioxy or ethylenedioxy, each of which is doubly linked, it being possible for tile alkylene or dioxyalkylene groups to be monosubstituted to tetrasubstituted, identically or differently, by fluorine, chlorine, trifluoromethyl, methyl, ethyl and/or n-propyl, or $R^1$ and $R^2$, together with the carbon atoms to which they are bonded, represent a fused furan, thiophene, pyrrole, oxazole, thiazole, imidazole, isoxazole, isothiazole, pyrazole, 1,2,3-oxadiazole, 1,2,3-thiadiazole, 1,2,3-triazole, pyridine, pyridazine, pyrazine, pyrimidine or 1,2,4-triazine ring, it being possible for these radicals to be monosubstituted or disubstituted, identically or differently, by fluorine, chlorine, bromine, cyano, nitro, amino, hydroxyl, formyl, carboxyl, carbamoyl, thiocarbomyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylstilphonlyl, trifluoromethyl, difluoromethoxy, trifluoromethoxy, difluoromethylthlio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminoethyl, methoxyiminoethyl and/or ethoxyiminoethyl and $R^3$ represents fluorine, chlorine, bromine, methyl, ethyl, n-propyl, isopropyl, n-butyl, sec-butyl, iso-butyl, tert-butyl or phenyl.

Particularly preferred in addition are compounds of the formula (Ib), in which $Hal^1$ represents fluorine, chlorine or bromine, $R^1$ represents fluorine, chlorine, bromine, methyl, ethyl, n-propyl, isopropyl, n-butyl, sec-butyl, iso-butyl, tert-butyl or phenyl, $R^2$ represents fluorine, chlorine, bromine, methyl, ethyl, n-propyl, isopropyl, n-butyl, sec-butyl, iso-butyl, tert-butyl or phenyl, or $R^1$ and $R^2$, together with the carbon atoms to which they are bonded, represent a fused furan, thiophene, pyrrole, oxazole, thiazole, imidazole, isoxazole, isothiazole, pyrazole, 1,2,3-oxadiazole, 1,2,3-thiadiazole, 1,2,3-triazole, pyridine, pyridazine, pyrazine, pyrimidine or 1,2,4-triazine ring, it being possible for these radicals to be monosubstituted or disubstituted, identically or differently, by fluorine, chlorine, bromine, cyano, nitro, amino, hydroxyl, formyl, carboxyl, carbamoyl, thiocarbamoyl, methyl, ethyl, n- or i-propyl, n-,i-, s- or t-butyl, methoxy, ethoxy, n- or i-propoxy, methyltihio, ethylthio, n- or i-propyltliio, methylsulphinyl, ethylsulphinyl, methylsulphonyl, ethylsulphonyl, trifluoromethyl, difluoromethoxy, trifluoromethoxy, difuoromethylthio, trifluoromethylthio, trifluoromethylsulphinyl or trifluoromethylsulplhonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, metlioxyiminoethyl and/or ethoxyiminoethyl, or $R^1$ and $R^2$ together represent a doubly bonded radical of the formula

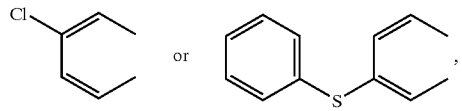

and $R^3$ represents fluorine, chlorine, bromine, methyl, ethyl, n-propyl, isopropyl, n-butyl, sec-butyl, iso-butyl, tert-butyl or phenyl.

The abovementioned meanings of the substituents can be combined with one another in any desired manner. In addition, individual definitions may also be omitted.

The nitrophenyl-sulphonylimidazoles shown in the following tables may be mentioned as examples of substances according to the invention.

TABLE 1

(Ic)

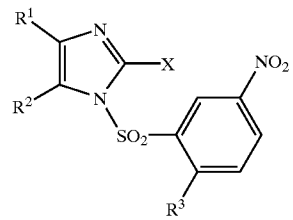

| $R^1$ | $R^2$ | $R^3$ | X |
|---|---|---|---|
| Cl | Cl | —CH$_3$ | Cl |
| Cl | Cl | —CH$_3$ | Br |

TABLE 1-continued
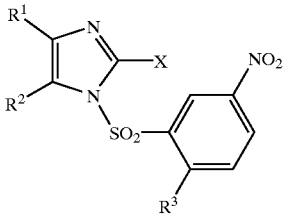
(Ic)
| R¹ | R² | R³ | X |
|---|---|---|---|
| —C₂H₅ | Cl | —CH₃ | Cl |
| —C₂H₅ | Br | —CH₃ | Br |
| —C₃H₇-n | Cl | —CH₃ | Cl |
| —CH₃ | F | —CH₃ | —CN |
| —CH₃ | 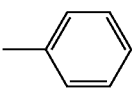 | —CH₃ | Br |
| Br | Br | —CH₃ | Br |
| Br | Br | —C₃H₇-n | Cl |
| Br | Br | 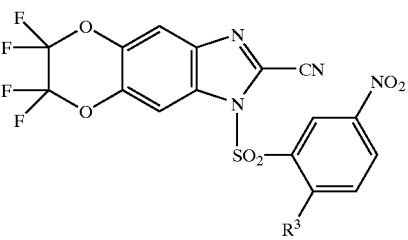 | Cl |
| Br | Br | F | Cl |
| Cl | Cl | Cl | —CN |
| CH₃ | Br | C₂H₅ | Cl |
| CH₃ | Br | —C₃H₇-n | Cl |
| CH₃ | Br | 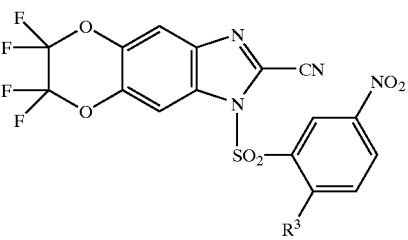 | Br |
TABLE 2
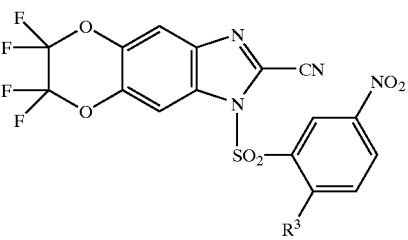
(Id)
R³ = C₂H₅
C₃H₇
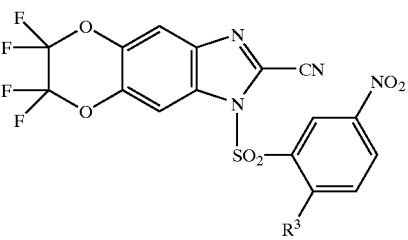
F
Cl
TABLE 3
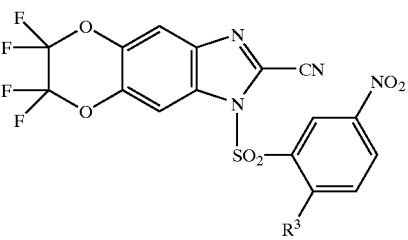
(Ie)
wherein
R³ represents the substituents mentioned in Table 2.
TABLE 4
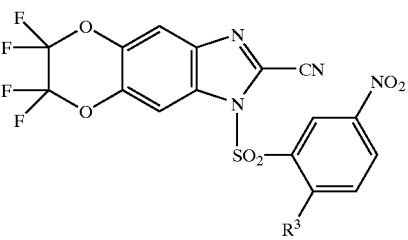
(If)
| R³ | X |
|---|---|
| —C₂H₅ | Cl |
| —C₂H₅ | Br |
| —C₂H₅ | —CN |
| —C₃H₇ | Cl |
| —C₃H₇-n | Br |
| —C₃H₇-n | —CN |
| 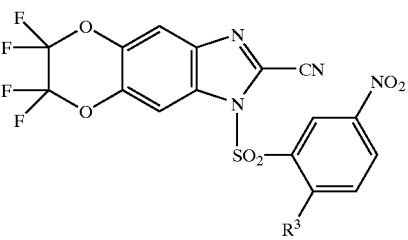 | Cl |
| 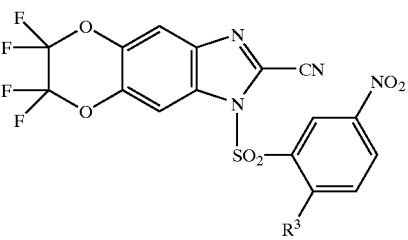 | Br |
| 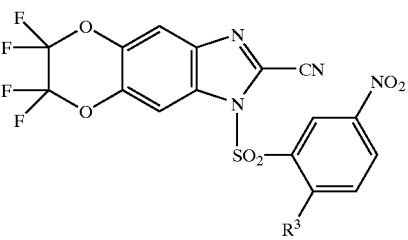 | —CN |
| F | Cl |
| F | Br |
| F | —CN |
| Cl | Cl |
| Cl | Br |
| Cl | —CN |

TABLE 5
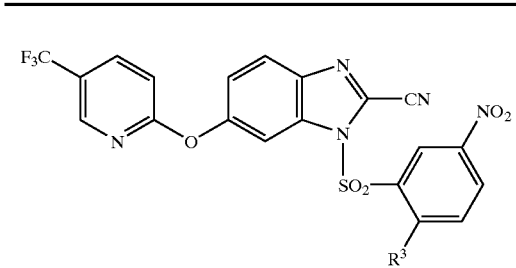
(Ig)
where
R³ represents the substituents mentioned in Table 2.
TABLE 6
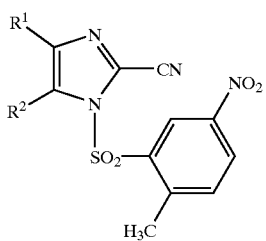
(Ih)
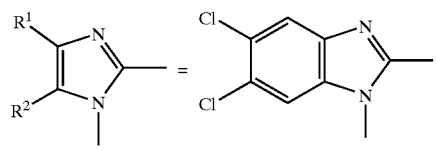
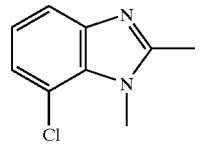
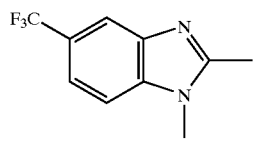
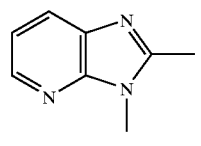
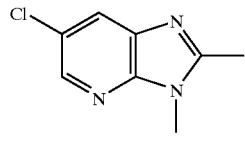
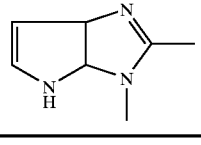
TABLE 7
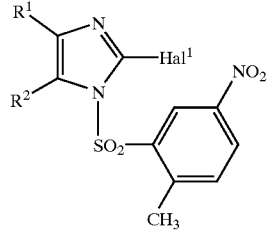
(Ii)
| | Hal¹ |
|---|---|
| | Cl |
| | Cl |
| | Cl |
| | Br |
| | Br |
| | Br |
If 2,5-dibromo-4-methyl-1H-imidazole and 2-methyl-5-nitrobenzenesulphonyl chloride are used as starting materials, the course of the process according to the invention can be illustrated by the following equation.
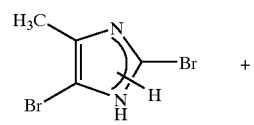 +

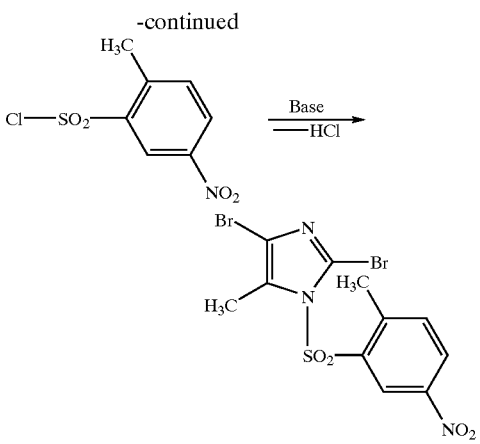

The imidazole derivatives required as starting materials for carrying out the process according to the invention are generally defined by the formula (II). In this formula, $R^1$, $R^2$ and X preferably have those meanings which have already been mentioned in connection with the description of the substances, according to the invention, of formula (I) as being preferred for the substituents.

The compounds of the formula (II) may be present in the following two tautomeric forms.

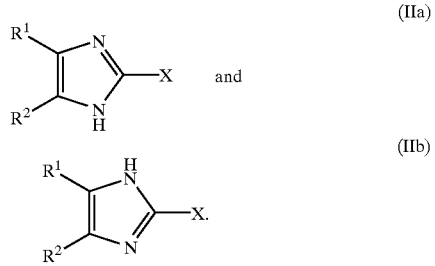

If the molecular unit

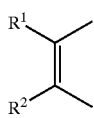

is symmetrical, the tautomeric forms are identical. In the reaction, according to the invention, with nitrobenzene-sulphonyl halides of the formula (III), only one specific end product of the formula (1) is thus formed in each case, and is formed independently of which of the two tautomeric forms reacts.

If the molecular unit

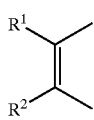

is asymmetrical, the two tautomeric forms are not identical. In the reaction, according to the invention, with nitrobenzene-sulphonyl halides of the formula (III), end products of the formula (1) which are derived from the tautomeric forms of the formulae (IIa) and/or (IIb) can thus form. If both tautomers react, end products of the formula (I) are obtained in the form of mixtures.

The imidazole derivatives of the formula (II) are known or can be prepared by known methods (cf. WO 97-06171, Chem. Ber. 85, (1952) 1012–1020), J. Med. Chem. 34 (1991), 1110–1116 and J. Chem. Soc. 1965, 3017–3021).

The nitrobenzene-sulphonyl halides furthermore required as starting materials for carrying out the process according to the invention are generally defined by the formula (III). In this formula, $R^3$ preferably has those meanings which have already been mentioned in connection with the description of the substances, according to the invention, of the formula (I) as being preferred for these substituents. Hal also preferably represents chlorine or bromine.

The nitrobenzene-sulphonyl halides of the formula (III) are known or can be prepared by known methods (cf. EP-A 0 238 824).

All customary inorganic or organic bases are suitable as acid acceptors for carrying out the process according to the invention. Alkaline earth metal or alkali metal hydrides, hydroxides, amides, alcoholates, acetates, carbonates or bicarbonates, such as, for example, sodium hydride, sodium amide, sodium methylate, sodium ethylate, potassium tert-butylate, sodium hydroxide, potassium hydroxide, sodium acetate, potassium acetate, calcium acetate, sodium carbonate, potassium carbonate, potassium bicarbonate or sodium bicarbonate, furthermore ammonium compounds, such as ammonium hydroxide, ammonium acetate or ammonium carbonate, and tertiary amines, such as triniethiylamiiine, triehliylamine, tributylamine, N,N-dimethylaniilinie, N,N-dimethyl-benlzylaminie, pyridine, N-methylpiperidine, N-methylmorpholine, N,N-dimethylaniinopyridine, diazobicyclooctane (DABCO), diazabicyclononene (DBN) or diazabicycloundecene (DBU), may preferably be used.

All inert organic solvents are suitable as diluents for carrying out the process according to the invention. Aliphatic, alicyclic or aromatic hydrocarbons such as, for example, petroleum ether, hex ane, heptane, cyclohexane, methylcycloliexane, benzene, toluene, xylene or decalin; halogenated hydrocarbons, such as, for example, chlorobenzene, dichlorobenzene, dichloromethane, chloroform, tetrachloromethane, dichloroethane or tri-cliloroethane; ethers such as diethyl ether, diisopropyl ether, methyl t-butyl ether, methyl t-amyl ether, dioxane, tetrahydrofuran, 1,2-dimethoxyethanie, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethyl-phosphorotriamide; esters, such as methyl acetate or ethyl acetate; sulphoxides, such as dimethyl sulphoxide; sulphones, such as sulpholane, or amines, such as pyridine, may preferably be used.

When carrying out the process according to the invention, the reaction temperatures can be varied within a relatively large range. In general, temperatures between 0° C. and 150° C., preferably temperatures between 10° C. and 120° C., are employed.

The process according to the invention is generally carried out under atmospheric pressure. However, it is also possible to employ superatmospheric or reduced pressure.

When the process according to the invention is carried out, in general 1 to 1.5 mol of nitrobenzene-sulplhonyl halide of the formula (III) and an equivalent amount or an excess of acid acceptor are used per 1 mol of imidazole derivative of the formula (II). The working up is effected by customary methods. In general, water is added to the reaction mixture, the mixture formed is extracted several times with an organic solvent slightly soluble in water, and the combined organic phases are dried and evaporated down. The substances obtained can optionally be purified by customary methods, such as chromatography or recrystallization.

The active substances according to the invention are suitable for controlling vegetable pests and can therefore be used for controlling undesired microorganisms, such as fungi or bacteria, in crop protection and in material protection.

Fungicides can be used in crop protection for controlling plasmodiophoromycetes, Oomycetes, Chytridiomycetes, Zygomycetes, Ascomycetes, Basidiomycetes, Deuteromycetes.

Bactericides can be used used in crop protection for controlling Pseudomonadaceae, Rhizobiaceae, Enterobacteriaceae, Corynebacteriaceae and Streptomycetaceae.

Some pathogens of fungal and bacterial diseases which are included under the general terms listed above may be mentioned by way of example without imposing any limitation:

Xanthomonas species, such as *Xanthomonas campestris* pv. *oryzae;*

Pseudomonas species, such as *Pseudomonas syringae* pv. *lachryrnans;*

Ervinia species, such as *Erwinia amylovora;*

Pythium species, such as *Pythium ultimum;*

Phyiophtlora species, such as *Phytophthora infestans;*

Pseudoperonospora species, such as *Pseudoperonospora humuli* or *Pseudoperono-spora cubensis;*

Plasniopara species, such as *Plasmopara viticola;*

Bremia species, such as *Bremia lactucae;*

Peronospora species, such as *Peronospora pisi* or *P. brassicae;*

Erysiphe species, such as *Erysiphe graminis;*

Sphaerotheca species, such as *Sphaerotheca fuliginea;*

Podosphaera species, such as, for example, *Podosphaera leucotriclia;*

Venturia species, such as *Venturia inaequalis;*

Pyrenophora species, such as *Pyrenophora teres* or *P. graminea (Conidia fonn: Drechslera, Syn: Helminthosporium);*

Cochliobolus species, such as *Cochliobolus sativus (Conidia form: Drechslera, Syn: Helminthosporium);*

Uromyces species, such as *Uromyces appendiculatus;*

Puccinia species, such as *Puccinia recondita;*

Sclerotinia species, such as *Sclerotinia sclerotiorum;*

Tilletia species, such as *Tilletia caries;*

Ustilago species, such as *Ustilago nuda* or *Ustilago avenae;*

Pellicularia species, such as *Pellicularia sasakii;*

Pyricularia species, such as *Pyricularia oryzae;*

Fusarium species, such as *Fusarium culmorum;*

Botrytis species, such as *Botrytis cinerea;*

Septoria species, such as *Septoria nodorum;*

Leptosphaeria species, such as *Leptosphaeria nodorum;*

Cercospora species, such as *Cercospora canescens;*

Alternaria species, such as, for example, *Altemaria brassicae;*

Pseudocercosporella species, such as *Pseudocercosporella herpotrichoides.*

The good plant tolerance of the active substances in the concentrations required for controlling plant diseases permits the treatment of above-ground plant parts, of plant material and seed and of the soil.

The active substances according to the invention can be particularly successfully used for controlling diseases in viticulture, fruit cultivation and vegetable cultivation, such as against Venturia, Podosphaera, and Plasmopara species. Rice diseases, such as Pyricularia species, are also successfully controlled.

In material protection, the substances according to the invention can be used for the protection of technical materials from attack and destruction by undesired microorganisms.

In the present context, technical materials are to be understood as meaning nonliving materials which have been prepared for use in industry. For example, technical materials which are to be protected by active substances according to the invention against microbial change or destruction may be adhesives, glues, paper and cardboard, textiles, leather, wood, coating materials and plastics articles, cooling lubricants and other materials which may be attacked or decomposed by microorganisms. Parts of production plants, for example cooling circulations, which may be impaired by multiplication of organisms may also be mentioned among the materials to be protected. In the present invention, preferably adhesives, glues, papers and cardboards, leather, wood, coating materials, cooling lubricants and heat-transfer liquids may be mentioned as technical materials, particularly preferably wood.

For example, microorganisms of the following genera may be mentioned:

Altemaria, such as *Altemaria tenuis,*

Aspergillus, such as *Aspergillus niger,*

Chactomium, such as *Chaetomium globosum,*

Coniophora, such as *Coniophora puetana,*

Lentinus, such as *Lentinus tigrinus,*

Penicillium, such as *Penicillium versicolor,*

Aureobasidium, such as *Aureobasidiuin pullulans,*

Sclerophomiia, such as *Scleropho ma pityophila,*

Trichoderma, such as *Trichoderma viride,*

Esclierichia, such as *Escherichia coli,*

Pseudomonas, such as *Pseudomonas aeruginosa,*

Staphylococcus, such as *Staphylococcus aureus.*

The active substances according to the invention which have good plant tolerance and advantageous toxicity with respect to warm-blooded animals are also suitable for controlling animal pests, in particular insects, arachnids and nematodes, which occur in agriculture, in forests, in horticulture, in the protection of stored goods and materials and in the hygiene sector or in the area of veterinary medicine. The substances are effective against normally sensitive and resistant species and against pests in all or individual stages of development. The abovementioned animal pests include:

From the order of the Isopoda, for example *Oniscus asellus, Armadillidium vulgare, Porcellio scaber.*

From the order of the Diplopoda, for example *Blaniulus guttulatus.*

From the order of the Chilopoda, for example *Geophilus carpophagus,* Scutigera spec.

From the order of the Symphyla, for example *Scutigerella immaculata.*

From the order of the Thysanura, for example *Lepisma saccharina.*

From the order of the Collembola, for example *Onychiurus armatus*.

From the order of the Orthoptera, for example *Blatta orientalis, Periplaneta americana, Leticophaea maderae, Blattella germanica, Acheta domesticus,* Gryllotalpa spp., *Locusta migratoria migratorioides, Melanoplus differentialis, Schistocerca gregaria.*

From the order of the Dermaptera, for example *Forficula auricularia.*

From the order of the Isoptera, for example Reticulitermes spp.

From the order of the Anoplura, for example *Pediculus humanus corporis,* Haematopinus spp., Linognathus spp.

From the order of the Mallophaga, for example Trichodectes spp., Damalinea spp.

From the order of the Thysanoptera, for example *Hercinothrips femoralis, Thrips tabaci.*

From the order of the Heteroptera, for example Eurygaster spp., *Dysdercus intermedius, Piesma quadrata, Cimex lectularius, Rhodnius prolixus,* Triatoma spp.

From the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiplium avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., Psylla spp.

From the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuchniella, Galleria mclonella, Tineola bisselliella, Tinea pellionella, Hofmannophila pseudospretella, Cacoecia podania, Capua rcticulana, Choristoneura fumiferana, Clysia ambiguella, Homona magnanima, Tortrix viridana.*

From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderna spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon soistitialis, Costelytra zealandica.*

From the order of the Hymenoptera, for example Diprion spp., Hoplocampa spp., Lasius spp., *Monomonrum pharaonis,* Vespa spp.

From the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Osciniella frit,* Phorbia spp., *Pegomyia hyoscyami, Ceratitis capitata, Dacus oleae, Tipula paludosa.*

From the order of the Siphonaptera, for example *Xenopsylla cheopis,* Ceratophyllus spp.

From the order of the Arachnida, for example *Scorpio maurus, Latrodectus mactans.*

From the order of the Acarina, for example *Acarus siro,* Argas spp., Ornithodoros spp., *Dennanyssus gallinae, Eriophyes ribis, Phyllocoptruta oleivora,* Boophilus spp., Rhipicephalus spp., Aniblyomma spp., Hyalomma spp., Ixodes spp., Psoroptes spp., Chorioptes spp. Sarcoptes spp., Tarsonemus spp., *Bryobia praetiosa,* Panonyclius spp., Tetranyclius spp.

The phytoparasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp., Trichodorus spp.

The substances which can be used according to the invention can be particularly successfully employed for controlling plant-damaging mites, such as against the bean spider mite (*Tetranychus urticae*), or for controlling plant-damaging insects, such as against the caterpillars of the diamond-back moth (*Plutella maculipennis*), the larvae of the horseradish leaf beetle (*Phaedon cochleariae*), and the green rice cicada (*Nephotettix cincticeps*).

The substances which may be used according to the invention act not only against plant pests, hygiene pests and pests of stored goods but also in the veterinary medical sector against animal parasites (ectoparasites), such as scale ioxodid ticks, argasidae, mange mites, trombiidae, flies (biting and licking), parasitic fly larvae, lice, biting lice, bird lice and fleas. These parasites include:

From the order of the Anoplurida, for example Haematopinus spp., Linognathus spp., Pediculus spp., Phtirus spp., Solenopotes spp.

From the order of the Mallophagida and the suborders Amblycerina and Ischnocerina, for example Trimenopon spp., Menopon spp., Trinoton spp., Bovicola spp., Wenieckiella spp., Lepikentron spp., Damalina spp., Trichodectes spp., Felicola spp.

From the order of Diptera and the suborders Nematocerina and Brachycerina, for example, Aedes spp., Anoplieles spp., Culex spp., Simulium spp., Eusimulium spp., Phlebotomus spp., Lutzomyia spp., Culicoides spp., Clirysops spp., Hybomitra spp., Atylotus spp., Tabanus spp., Haeniatopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophiaga spp., Oestrus spp., Hypoderma spp., Gasterophilus spp., Hippobosca spp., Lipoptena spp., Melophagus spp.

From the order of the Siphonapterida, for example Pulex spp., Ctenocephalides spp., Xenopsylla spp., Ceratophyllus spp.

From the order of the Heteroptenrda, for example Cimex spp., Triatoma spp., Rhodnius spp., Panstrongylus spp.

From the order of the Blattarida, for example *Blatta orientalis, Periplaneta americana, Blattela gernanica,* Supella spp.

From the subclass of the Acaria (Acarida) and the orders of the Meta- and Mesostigmata, for example Argas spp., Ornithodorus spp., Otobius spp., Ixodes spp., Amblyomma spp., Boophilus spp., Derrnacentor spp., Haemophysalis spp., Hyalomma spp., Rlhipicephalus spp., Dermanyssus spp., Raillietia spp., Pneumonyssus spp., Stemostoma spp., Varroa spp.

From the order of the Actinedida (Prostigmata) and Acaridida (Astigmata), for example Acarapis spp., Cheyletiella spp., Ornitliocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp.

The active substances according to the invention are also suitable for increasing the harvest yield. In addition, they have low toxicity and possess good plant tolerance.

Depending on their respective physical and/or chemical properties, the active substances can be converted into the customary formulations, such as solutions, emulsions, suspensions, powders, foams, pastes, granules, aerosols, very finely encapsulated forms in polymeric substances and in coating materials for seed and ULV cold and warm mist formulations.

These formnulations are prepared in a known manner, for example by mixing the active substances with extenders, that is to say liquid solvents, liquefied gases under pressure and/or solid carriers, optionally with the use of surfactants, that is to say emulsifiers and/or dispersants and/or form-producing compositions. In the case of the use of water as an extender, for example, organic solvents may also be used as auxiliary solvents. Suitable liquid solvents are essentially: aromatics, such as xylene, toluene or alkylnaplithalenes, chlorinated aromatics or chlorinated aliphatic hydrocarbons, such as chlorobenzenes, chloroethylenes or methylene chloride, aliphatic hydrocarbons, such as cyclohexane or paraffins, e.g. mineral oil fractions, alcohols such as butanol or glycol, and their ethers and esters, ketones, such as acetone, methyl ethyl ketone, methyl isobutyl ketone or cyclohexanone, strongly polar solvents, such as dimethylformamide and dimethyl sulphoxide, and water. Liquefied gaseous extenders or carriers are those liquids which are gaseous at normal temperature and under normal pressure, for example aerosol propellants, such as halogenohydrocarbons and butane, propane, nitrogen and carbon dioxide. Suitable solid carriers are: for examnple, crushed natural minerals, such as kaolins, aluminas, talc, chalk, quartz, attapulgite, montmorillonite or diatomaceous earth, and crushed synthetic minerals, such as finely divided silica, alumina and silicates. Suitable solid carriers for granules are: for examnple, crushed and fractionated natural minerals, such as calcite, marble, pumice, sepiolite, dolomite, and synthetic granules of inorganic and organic powders and granules of organic material, such as sawdust, coconut shells, maize cobs and tobacco stems. Suitable emulsifiers and/or form-producing compositions are: for example, non-ionic and anionic emulsifiers, such as polyoxyethiylene fatty acid esters, polyoxyethylene fatty alcohol ethers, e.g. alkylaryl polyglycol ethers, alkylsulphonates, alkylsulphates, arylsulplionates and protein hydrolysis products. Suitable dispersants are: for example, ligninsulplite waste liquors and methylcellulose.

Adherents, such as carboxyrnethylcellulose, natural and synthetic pulverulent, granular or latex-like polymers may be used in the formulations, such as gum arabic, polyvinyl alcohol, polyvinyl acetate and natural phospholipids, such as kephalins and lecithins, and synthetic phospholipids. Further additives may be mineral and vegetable oils.

Colorants, such as inorganic pigments, e.g. iron oxide, titanium oxide, Prussian blue, and organic dyes, such as alizarin, azo and metal phthalocyanine dyes, and trace nutrients, such as salts of iron, manganese, boron, copper, cobalt, molybdenum and zinc, may be used.

The formulations contain in general between 0.1 and 95 per cent by weight of active substance, preferably between 0.5 and 90%.

Depending on their respective physical and/or chemical properties, the active substances can be converted into the customary formulations, such as solutions, emulsions, suspensions, powders, foams, pastes, granules, aerosols, very finely encapsulated forms in polymeric substances and in coating materials for seed, and ULV cold mist and warm mist formulations.

The active substances according to the invention can be used, as such or in their formulations, also as a mixture with known fungicides, bactericides, acaricides, nematicides or insecticides, in order, for example, to broaden the action spectrum or to prevent the development of resistance. In many cases, synergistic effects are obtained, i.e. the activity of the mixture is greater than the activity of the individual components.

Suitable components of the mixture are, for example, the following compounds:

Fungicides:
  aldimorph, ampropylfos, ampropylfos potassium, andoprim, anilazine, azaconazole, azoxystrobin,
  benalaxyl, benodanil, benomyl, benzamacril, benzamacryl-isobutyl, bialaphos, binapacryl, biphenyl, bitertanol, blasticidin-S, bromuconazole, bupirimate, buthiobate,
  calcium polysulphide, capsimycin, captafol, captan, carbendazim, carboxin, carvon, chinomethionate (quinomethionate), chlobenthiazone, chlorfenazole, chloroneb, chloropicrin, chlorothalonil, chlozolinate, clozylacon, cufraneb, cymoxanil, cyproconazole, cyprodinil, cyprofuiram,
  debacarb, dichlorophen, diclobutrazol, diclofluanid, diclomezine, diclorane, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
  ediphenphos, epoxiconazole, etaconazole, ethirimol, etridiazole,
  famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazol, flusulfamide, flutolanil, flutriafol, folpet, fosetyl aluminium, fosetyl sodium, fthalide, fuberidazole, furalaxyl, furametpyr, furcarbonil, furconazole, furconazol-cis, furmecyclox,
  guazatine,
  hexachlorobenzene, hexaconazole, hyinexazol,
  imazalil, iImnibenconiazole, iminoctadine, iminoctadine albesilate, iminoctadine triacetate, iodocarb, ipconazole, iprobenfos (UBP), iprodione, irumamycin, isoprothiolane, isovaledione,
  kasugamycin, kresoxime-methIyl, Copper formulations, such as: copper hydroxide, copper naphthenate, copper oxychloride, copper sulphate, copper oxide, oxine-copper and Bordeaux mixture,
  mancopper, mancozeb, maneb, meferimzone, mepanipyrim, mepronil, metalaxyl, metconazol, methasulfocarb, methfuroxam, metiram, metomeclam, metsulfovax, mildiomycin, myclobutanil, myclozolin,
  nickel dimethyidithiocarbamate, nitrothal-isopropyl, nuarimol,
  ofurace, oxadixyl, oxamocarb, oxolinicacide, oxycarboxim, oxyfenthiine, paclobutrazol, pefurazoate, penconazole, pencycuron, phosdiphen, pimaricin, piperalin, polyoxin, polyoxorim, probenazole, prochloraz, procymidon, propamnocarb, propanosine sodium, propiconazole, propineb, pyrazophos, pyrifenox, pyrimethanil, pyroquilon, pyroxyfur, quinconazole, quintozene (PCNB), Sulphur and sulphur formulatons, tebuconazole, tecloflalamn, tecnazene, tetcyclacis, tetraconazole, thiabendazol, thicyofen, thilfluzanide, tlliophaniate-methyl, thirain, tioxymid, tolclofosmethyl, tolylfluanlid, triadiniefon, triadimenol, triazbutil, triazoxide, trichiamide, tricyclazole, tridemorph, triflumizole, triforine, triticonazol, uniconazole, validamycin A, vinclozolin, viniconazole, zarilamid, zineb, ziram and Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS, 6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-diclorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-2-mnethyl-4'-trifluoromethoxy-4'-trifluoromethyl-1,3-tiliazole-5-carboxanilide, 2,2-dichloro-N-[1-(4-chlorophenyl)-etliyl]-1-ethyl-3-methyl-cyclopropanecarboxamide, 2,6-dichloro-5-(methylthio)-4-pyrimidinyl thiocyanate, 2,6-dichloro-N-(4-trifluoromnethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methyletihyl)-sulphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol(OPP), 3,4-dichloro-1-[4-(difluoromethoxy)-phenyl]-1H-pyrrole-2,5-dione, 3,5-dichloro-N-[cyan[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyan-N,N-dimethyl-5-(4-methylphenyl)-1H-imidazole-1-sulphonamide, 4-methyl-tetrazolo[1,5-a]-quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-9-carboxylic acid 2-[(phenylamino)-carbonyl]-hydrazide, bis-(1-methylethyl)-3-methyl-4-[(3-methylbenzoyl)-oxy]-2, 5-thiophene dicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl[(4-chlorophenyl)-azo]-cyanoacetate, potassium bicarbonate, methlaietetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(cliloroacetyl)-N-(2,6-dimetihylphenyl)-DL-alaninate, N-(2,3-dichloro-4-hydroxypherlyl)-1-metliyl-cyclohexancarboxaniide.

N-(2,6-dirnethylphenyl)-2-methoxy-N-(tetrahydro-2-oxo-3-furanyl)-acetamide,

N-(2,6-dimetliylplcyi)-2-methoxy-N-(tetrahydro-2-oxo-3-thienyl)-acetamide,

N-(2-clhloro-4-tiitroplenyl)-4-mcthyl-3-nitro-benzolsulpllonamide,

N-(4-cycloliexylphenyl)-1,4,5,6-tetrahydro-2-pyrimidinamine,

N-(4-hexylplhenyl)-1,4,5,6-tetralydro-2-pyrimidinaniine,

N-(5-chloro-2-methylphenyl)-2-netiloxy-N-(2-oxo-3-oxazolidinyl)-acetamide,

N-(6-metlhoxy)-3-pyridinyl)-cyclopropanecarboxamide,

N-[2,2,2-trichloro-1-[(chloroacetyl)-amino]-ethyl]-benzamide,

N-[3-chloro-4,5-bis-(2-propinyloxy)-phenyl]-N'-methoxy-methaneimidoamide,

N-formyl-N-hydroxy-DL-alanine sodium salt,

O,O-diethyl-[2-(dipropylamino)-2-oxocthyl]-ethylphosphoramidothioate,

O-methyl S-phenyl phenylpropylphosphoramidothioate,

S-methyl 1,2,3-benzothiadiazole-7-carbothioate,
spiro[2H]-1-benzopyran-2,1'(3'H)-isobenzofuran]-3'-one, Bactericides:
 bronopol, dichlorophen, nitrapyrin, nickel dimethyidithiocarbamate, kasugamycin, octhilinone, furancarboxylic acid, oxytetracycline, probenazole, streptomycin, tecloftalam, copper sulphate und other copper formulations.

Insecticides/Acaracides/Nematicides:
 abamectin, acephate, acrinathrin, alanycarb, aldicarb, alphamethrin, amitraz, avermectin, AZ 60541, azadirachtin, azinphos A, azinphos M, azocyclotin,
 bacillus thuringiensis, 4-Bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben,
 cadusafos, carbaryl, carbofuran, carbophenothion, carbosulphan, cartap, chloethocarb, chlorethioxyfos, clilorfenapyr, chlorfenvinpihos, chliorfluazuron, chlonnephos, N-[(6-cilloro-3-pyriditlyl)-niethyl]-N'-cyano-N-methyl-ethaneimidoamide, chlorpyrifos, chlorpyrifos M, cis-resmethrin, clocythrin, clofentezine, cyanophos, cycloprothrin, cyflutlirin, cylialotlirin, cyhexatin, cypermethrin, cyromazine,
 deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton,
 edifenphos, emamectin, esfen valerate, ethiofencarb, ethion, ethofenprox, ethoprophos, etrimphos,
 fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, ftirathiocarb,
 HCH, heptenophos, hexaflumuron, hexythiazox,
 imidacloprid, iprobenfos, isazophos, isofenphos, isoprocarb, isoxathion, ivermectin, lamnda-cyhalothrin, lufenuron,
 malathion, mecarbam, mevinphos, mesulphenphos, metaldehyde, methacrifos, methamidophos, methidathion, methiocarb, methomyl, metolcarb, milbemectin, monocrotophos, moxidectin,
 naled, NC 184, nitenpyram
 omethoate, oxamyl, oxydemethon M, oxydeprofos,
 parathion A, parathion M, permethrin, phenthoate, phorate, phosalone, phosmet, phosphamidon, plioxim, pirimicarb, pirimiphos M, pirimiphos A, profenophos, promecarb, propaphos, propoxur, prothiophos, prothoate, pymetrozine, pyrachlophos, pyridaphenthion, pyresnietlirin, pyrethrum, pyridaben, pyrimidifen, pyriproxifen,
 quinalphos,
 salithion, sebufos, silafluofen, sulphotep, suiprofos,
 tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb,
 vamidothion, XMC, xylylcarb, zetamethrin.

A mixture with other known active substances, such as herbicides, or with fertilizers and growth regulators, is also possible.

The active substances can be used as such, in the form of their formulations or the use forms prepared therefrom, such as ready-to-use solutions, suspensions, wettable powders, pastes, soluble powders, dusting agents and granules. They are used in a customary manner, for example by pouring, spraying, atomizing, broadcasting, dusting, foam application, brushing, etc. It is also possible to apply the active substances by the Ultra-Low-Volume method or to inject the active substance formulation or the active substance itself into the soil. The seed of the plants may also be treated.

When the active substances according to the invention are used as fungicides, the application rate may be varied within a relatively large range, depending on the method of application. In the treatment of plant parts, the application rates of active substance are in general between 0.1 and 10,000 g/ha, preferably between 10 and 1000 g/ha. In the treatment of seed, the application rates of active substance are in general between 0.001 and 50 g per kilogram of seed, preferably between 0.01 and 10 g per kilogram of seed. In the treatment of the soil, the application rates of active substance are in general between 0.1 and 10,000 g/ha, preferably between 1 and 5000 g/ha.

The compositions used for protecting technical materials contain the active substances in general in an amount of 1 to 95%, preferably of 10 to 75%.

The use concentrations of the active substances according to the invention depend on the type and occurrence of the microorganisms to be controlled and on the composition of the material to be protected. The optimal amount for use can be determined by test series. In general, the use concentrations are in the range from 0.001 to 5% by weight, preferably from 0.05 to 1.0% by weight, based on the material to be protected.

The activity and the action spectrum of the active substances to be used according to the invention in material protection or of the compositions, concentrates or very generally formulations which can be prepared therefrom can be increased if optionally further antimicrobial compounds, fungicides, bactericides, herbicides, insecticides or other active substances are added for increasing the action spectrum or achieving special effects, such as, for example, additional protection from insects. These mixtures may have a broader action spectrum than the compounds according to the invention.

Even when used against animal pests, the substances according to the invention may be present as a mixture with synergistic agents in commercial formulations and in the use forms prepared from these formulations. Synergistic agents are compounds by means of which the action of the active substances is increased without the added synergistic agent itself having to be actively effective.

The active substance content of the use forms prepared from the commercial formulations may vary within wide ranges. The active substance concentration of the use forms may be from 0.0000001 to 95% by weight of active substance, preferably between 0.0001 and 1% by weight.

Application is effected in a customary manner adapted to one of the use forms.

The preparation and use of substances according to the invention are illustrated by the following examples.

PREPARATION EXAMPLE

Example 1

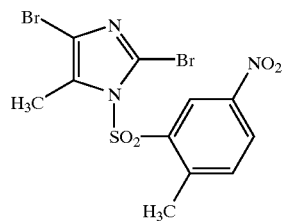

1.4 g (10 mmol) of potassium carbonate are added to a solution of 1.7 g (7 mmol) of 2,5-dibromo-4-methyl-1H-imidazole in 40 ml of acetonitrile at room temperature. The mixture is stirred for 10 minutes at room temperature, and 1.7 g (7 mmol) of 2-methyl-5-nitro-benzenesulphonyl chloride are then added. Stirring is carried out for a further 20 hours at room temperature and the reaction mixture is then poured onto 100 ml of water. The mixture formed is extracted twice with 50 ml of diethylether in each case. The combined organic[]phases are dried over sodium sulphate and then evaporated down under reduced pressure. The remaining residue is chromatographed on silica gel using methylene chloride as mobile phase. 1.6 g (51% of theory) of 1-(2-methyl-5-nitro-benzenesulphonyl)-2,4-dibromo-5-methyl-1H-imidazole are obtained in this manner in the form of a colorless solid substance of melting point 187 to 189° C.

The substances shown in Table 8 below are also prepared by the abovementioned methods.

TABLE 8-continued

General structure (I):

R¹, R² on imidazole ring; N-SO₂-phenyl with NO₂ and R³ substituents; position 2 bears X.

| Example No. | R¹, R² imidazole structure | Phenyl-SO₂ group (R³, NO₂) | X | Melting point (° C.) |
|---|---|---|---|---|
| 6 | 5,6-difluoromethylenedioxy-benzimidazole, N-methyl | 3-methyl-4-NO₂-phenyl (H₃C, NO₂) | —CN | ¹H-NMR-Sprectrum (CDCl₃, TMS): δ = 2.66 (s, 3H. CH₃), 7.55 (s, 2H, arom. prot.), 7.62 (d, 1H, J = 8.4 Hz, arom. prot.); 7.71 (s, 1H, arom. prot.); 8.49 (d, 1H, J = 8.4 Hz, arom. prot.); 9.12 (s, 1H, arom. prot.) ppm |
| 7 | 4-Cl-5-phenyl-2-methyl-imidazole, N-methyl | 3-methyl-4-NO₂-phenyl | Br | 66–72 |
| 8 | 4,5-dibromo-2-methyl-imidazole, N-methyl | 3-methyl-4-NO₂-phenyl | Br | 130–136 |

USE EXAMPLES

Example A

Phytophthora Test (Tomatoes)/protective

Solvent: 47 parts by weight of acetone

Emulsifier: 3 parts by weight of alkylaryl polyglycol ether

For the preparation of an expedient fonnulation of active substance, 1 part by weight of active substance is mixed with the stated amount of solvent and emulsifier and the concentrate is diluted to the desired concentration with water.

To test for protective activity, young plants are sprayed with the fornulation of active substance at the stated application rate. After the spray coating has dried on, the plants are inoculated with an aqueous spore suspension of phytophthora infestans. The plants are then placed in an incubation cabin at about 20° C. and 100% relative humidity.

The evaluation is carried out 3 days after the inoculation. 0% means an efficiency which corresponds to that of the control, while an efficiency of 100% means that no attack is observed.

Active substances, application rates and test results are shown in the table below.

TABLE A

Phytophthora Test (tomatoes)/protective

| Active substance | Application rate of active substance in g/ha | Efficiency in % |
|---|---|---|
| According to the invention (1): 4-Br-5-methyl-2-Br-imidazole N-sulfonyl-(3-methyl-4-nitrophenyl) derivative | 50 | 99 |

TABLE A-continued

Phytophthora Test (tomatoes)/protective

| Active substance | Application rate of active substance in g/ha | Efficiency in % |
|---|---|---|
| (3) 5-Chloro-2-chloro-1-(2-methyl-4-nitrophenylsulfonyl)benzimidazole | 50 | 96 |
| (7) 4-Chloro-2-bromo-5-phenyl-1-(2-methyl-4-nitrophenylsulfonyl)imidazole | 50 | 96 |

Disclosed in EP-A 0 238 824:

| | | |
|---|---|---|
| 2-methyl-1-(2-methyl-4-nitrophenylsulfonyl)imidazole | 50 | 85 |
| 2-chloro-1-(2-methyl-4-nitrophenylsulfonyl)benzimidazole | 50 | 71 |

Example B

Plasmopora Test (Grapevines)/protective

Solvent: 47 parts by weight of acetone

Emulsifier: 3 parts by weight of alkylaryl polyglycol ether

For the preparation of an expedient formulation of active substance, 1 part by weight of active substance is mixed with the stated amounts of solvent and emulsifier, and the concentrate is diluted to the desired concentration with water.

To test for protective activity, young plants are sprayed with the formulation of active substance at the stated application rate. After the spray coating has dried on, the plants are inoculated with an aqueous spore suspension of Plasmopara viticola and then remain for 1 day in an incubation cabinet at about 20° C. and 100% relative humidity. The plants are then placed in a greenhouse for 5 days at about 21° C. and about 90% relative humidity. The plants are then moistened and are placed in an incubation cabinet for 1 day.

The evaluation is carried out 6 days after the inoculation. 0% means an efficiency which corresponds to that of the control, while an efficiency of 100% means that no attack is observed.

Active substances, application rates and test results are shown in the table below.

TABLE B

Plasmopara test (grapevines)/protective

| Active substance | Application rate of active substance in g/ha | Efficiency in % |
|---|---|---|
| According to the invention | | |
| (3) 5-Chloro-2-chloro-1-(2-methyl-4-nitrophenylsulfonyl)benzimidazole | 50 | 92 |
| (7) 4-Chloro-2-bromo-5-phenyl-1-(2-methyl-4-nitrophenylsulfonyl)imidazole | 50 | 93 |

Example C

Phaedon Larvae Test

Solvent: 7 parts by weight of dimethylformamide

Emulsifier: 1 part by weight of alkylaryl polyglycol ether

For the preparation of an expedient fonnulation of active substance, 1 part by weight of active substance is mixed with the stated amounts of solvent and emulsifier, and the concentrate is diluted to the desired concentration with water.

Cabbage leaves (*Brassica oleracea*) are treated by immersion in the formulation of active substance of the desired concentration and infested with larvae of the horseradish beetle (*Phaedon cochleariae*) as long as the leaves are still moist.

After the desired time, the kill in % is determined. 100% means that all beetle larvae were killed; 0% means that no beetle larvae were killed.

Active substances, application rates and test results are shown in the table below.

TABLE C

Plant damaging insects

Phaedon larve test

| Active substances | Active substance concentration in % by weight | Kill in % after 7 d |
|---|---|---|
| According to the invention | | |
| (2) [structure: difluorodioxino-benzimidazole with CN and SO₂-aryl(CH₃, NO₂) substituents] | 0.1 | 100 |
| (5) [structure: difluorodioxino-benzimidazole with CN and SO₂-aryl(O₂N, CH₃) substituents] | 0.1 | 100 |

Example D

Plutella test

Solvent: 7 parts by weight of dimethylformamide

Emulsifier: 1 part by weight of alkylaryl polyglycol ether

For the preparation of an expedient formulation of active substance, 1 part by weight of active substance is mixed with the stated amounts of solvent and emulsifier, and the concentrate is diluted to the desired concentration with water.

Cabbage leaves (*Brassica oleracea*) are treated by immersion in the formulation of active substance of the desired concentration and infested with caterpillars of the diamondback moth (*Plutella xylostella*) as long as the leaves are still moist.

After the desired time, the kill in % is determined. 100% means that all caterpillars were killed; 0% means that no caterpillars were killed.

Active substances, application rates and test results are shown in the table below.

TABLE D

Plant-damaging insects

Plutella test

| Active substances | Active substance concentration in % by weight | Kill in % after 7 d |
|---|---|---|
| According to the invention | | |
| (2) [structure] | 0.1 | 100 |
| (5) [structure] | 0.1 | 100 |

TABLE E

Material protection test

To demonstrate the activity against fungi, the minimum inhibitory concentrations (MIC values) of compounds according to the invention are determined.

Active substances according to the invention are added, in concentrations of 0.1 mg/l to 5000 mg/l to an agar which is prepared using malt extract. Solidification of the agar is followed by contamination with pure cultures of test organisms. After storage for two weeks at 27° C. and 60 to 70% relative humidity, the minimum inhibitory concentration (MIC value) is determined. The MIC value characterizes the lowest concentration of active substance at which there is no growth at all of the microbe species used.

Active substances, test organisms and MIC values are shown in the table below.

Minimum inhibitory concentration (MIC value) in mg/l

| | Active substance according to Example No. | |
|---|---|---|
| Test organism | 2 | 5 |
| *Penicillium brevicaule* | 100 | 100 |
| *Chaetomium globosum* | 100 | 100 |
| *Aspergillus niger* | 200 | 200 |

What is claimed is:

1. A nitrophenyl-sulphonyl-imidazole of the formula (I)

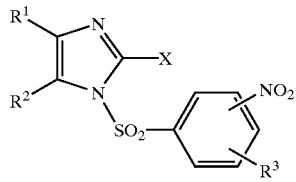

(I)

wherein

X represents fluorine, chlorine or bromine, $R^1$ represents fluorine, chlorine, bromine, straight-chain or branched alkyl having 1 to 6 carbon atoms or phenyl, $R^2$ represents fluorine, chlorine, bromine, straight-chain or branched alkyl having 1 to 6 carbon atoms or phenyl, and $R^3$ represents fluorine, chlorine, bromine, straight-chain or branched alkyl having 1 to 6 carbon atoms or phenyl.

2. A microbicidal composition comprising a microbicidally effective amount of a nitro-phenyl-sulphonyl-imidazole according to claim 1 in admixture with an inert diluent or carrier.

3. An insecticidal composition comprising an insecticidally effective amount of nitro-phenyl-sulphonyl-imidazole according to claim 1 in admixture with an inert diluent or carrier.

4. A method for controlling undesired microorganisms, which method comprises applying a microbicidally effective amount of nitro-phenyl-sulphonyl-imidazole according to claim 1 to the microorganisms or to their habitat.

5. A nitrophenyl-sulphonyl-imidazole of formula (I)

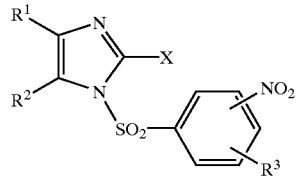

(I)

wherein

X represents bromine, $R^1$ represents bromine, $R^2$ represents methyl, and $R^3$ represents methyl.

* * * * *

UNITED STATES PATENT AND TRADEMARK OFFICE
CERTIFICATE OF CORRECTION

PATENT NO.      : 6,486,191 B2
DATED           : November 26, 2002
INVENTOR(S)     : Lutz Assmann et al.

It is certified that error appears in the above-identified patent and that said Letters Patent is hereby corrected as shown below:

<u>Title page,</u>
After Item "[76] Inventors:...", insert:

-- [73] Assignee: Bayer Aktiengesellschaft, Leverkusen (DE) --.

Please insert the following as Claim 5.

-- 5. A method for controlling insects, which method comprises applying an insecticidally effective amount of nitro-phenyl-sulphonyl-imidazole according to Claim 9 to the insects or to their habitat. --

Currently printed Claim 5 will become Claim 6.

Signed and Sealed this

Tenth Day of June, 2003

JAMES E. ROGAN
*Director of the United States Patent and Trademark Office*